(12) United States Patent
Zhou (10) Patent No.: US 8,554,314 B2
(45) Date of Patent: Oct. 8, 2013

(54) DEVICE AND METHOD TO DETECT THE SEVERITY OF ISCHEMIA AND HEART ATTACK RISK

(75) Inventor: Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 937 days.

(21) Appl. No.: 12/263,383

(22) Filed: Oct. 31, 2008

(65) Prior Publication Data

US 2010/0113954 A1 May 6, 2010

(51) Int. Cl.
*A61B 5/04* (2006.01)
(52) U.S. Cl.
USPC .......... 600/515; 600/508; 600/509; 600/510; 600/516; 600/517; 600/518
(58) Field of Classification Search
USPC ............ 600/508–510, 515–518; 607/17–26, 607/4, 5, 14
See application file for complete search history.

(56) References Cited

U.S. PATENT DOCUMENTS

| 5,560,370 | A | 10/1996 | Verrier et al. |
| 5,935,082 | A * | 8/1999 | Albrecht et al. ............... 600/515 |
| 6,983,183 | B2 * | 1/2006 | Thiagarajan et al. ......... 600/509 |
| 7,027,867 | B2 * | 4/2006 | Park et al. ........................ 607/25 |
| 7,512,438 | B2 * | 3/2009 | Fischell et al. ................ 600/509 |
| 2004/0215092 | A1 | 10/2004 | Fischell et al. |
| 2005/0256417 | A1 | 11/2005 | Fischell et al. |
| 2006/0116596 | A1 | 6/2006 | Zhou |
| 2008/0082133 | A1 | 4/2008 | Zhou |

* cited by examiner

*Primary Examiner* — Niketa Patel
*Assistant Examiner* — Mallika D Fairchild
(74) *Attorney, Agent, or Firm* — Stephen W. Bauer; Michael J. Ostrom (57) ABSTRACT

A device and method of detecting the severity of myocardial ischemia and heart attack risk is provided. The method includes obtaining an electrogram signal, determining T-wave measurements based on the electrogram signal, and determining ST segment measurements based on the electrogram signal. The method also includes identifying T-wave alternans based on the T-wave measurements and identifying ST segment changes based on the ST segment measurements. The method further includes correlating the T-wave alternans with the ST segment changes in order to detect a severity of ischemia.

35 Claims, 3 Drawing Sheets

DEVICE AND METHOD TO DETECT THE SEVERITY OF ISCHEMIA AND HEART ATTACK RISK

TECHNICAL FIELD

This disclosure relates generally to a method to detect the severity of myocardial ischemia and heart attack risk by correlating T-wave alternans with ST segment deviations.

BACKGROUND

Ischemia is a leading cause of mortality and involves oxygen starvation of the myocardium. Unfortunately, many episodes of myocardial ischemia do not cause excessive pain or other noticeable warning signs and often go undetected. If left untreated, myocardial ischemia can lead to the symptoms associated with acute coronary syndrome and the eventual cell death associated with acute myocardial infarction. Acute coronary syndrome generally includes the clinical symptoms associated with unstable angina, non-ST segment elevation or non-Q-wave myocardial infarction, and ST segment elevation or Q-wave myocardial infarction. In patients with ventricular dysfunction, sustained ischemia can also trigger sudden cardiac death and/or myocardial decompensation. Early detection of myocardial ischemia provides the opportunity for a wide range of effective therapies such as surgical revascularization, neural stimulation, and drug delivery to reduce cardiac workload or improve cardiac circulation.

An electrocardiogram (ECG) or electrogram (EGM) presents a PQRST waveform sequence that characterizes the cyclical cardiac activity of a patient. The ST segment, which is associated with the repolarization of the ventricles, is typically close in amplitude to the baseline (i.e., isoelectric amplitude) of the signal sensed between consecutive PQRST sequences. During episodes of myocardial ischemia, the ST segment amplitude deviates from the baseline. Accordingly, deviation in the ST segment is often used to identify an occurrence of myocardial ischemia.

The T-wave from the PQRST sequences can also correlate with ischemic conditions. Variations in the T-wave, called T-wave alternans (TWA) are rate dependent and occur once an increase in heart rate exceeds the kinetics of intracellular calcium cycling. Thus, TWA can occur during myocardial ischemia due to coronary occlusion (supply ischemia) or when blood demand surpasses blood supply (demanding ischemia). Also, TWA directly reflect the development of an arrhythmogenic substrate for ventricular tachyarrhythmia (VT/VF) through the mechanism of repolarization dispersion and creating unidirectional conduction for reentry formation.

SUMMARY

In one or more embodiments, a method of detecting the severity of myocardial ischemia is provided. The method includes obtaining an electrogram signal, determining T-wave measurements based on the electrogram signal, and determining ST segment measurements based on the electrogram signal. The method also includes identifying T-wave alternans based on the T-wave measurements and identifying ST segment changes based on the ST segment measurements. The method further includes correlating the T-wave alternans with the ST segment changes in order to detect a severity of ischemia.

Some embodiments of the invention provide an implantable medical device including a data collection module configured to obtain an electrogram signal and a data processing module coupled to the data collection module. The data processing module is configured to determine T-wave alternans based on the electrogram signal and to determine ST segment changes based on the electrogram signal. The data processing module is also configured to correlate the T-wave alternans with the ST segment changes in order to detect a severity of ischemia. The device also includes a therapy module coupled to the data processing module. The therapy module is configured to at deliver therapy and/or generate an alert indicating the severity of ischemia.

DESCRIPTION OF THE DRAWINGS

The above-mentioned features and objects of the present disclosure will become more apparent with reference to the following description taken in conjunction with the accompanying drawings wherein like reference numerals denote like elements and in which.

DETAILED DESCRIPTION

The present disclosure describes a method to detect the severity of myocardial ischemia and myocardial electrical/mechanical (E/M) dysfunction, for example related to sudden cardiac death, by correlating T-wave alternans with ST segment deviations. Some embodiments of the present disclosure can be used in conjunction with an implantable medical device (IMD).

The following detailed description is merely illustrative only and is not intended to limit the application and uses of the present disclosure. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present disclosure may be practiced in conjunction with any number of medical devices and therapies and that the system described herein is merely one exemplary application.

For the sake of brevity, conventional techniques related to IMD sensor signal processing, the adjustment and control of IMD therapy signals, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

Figure 2:
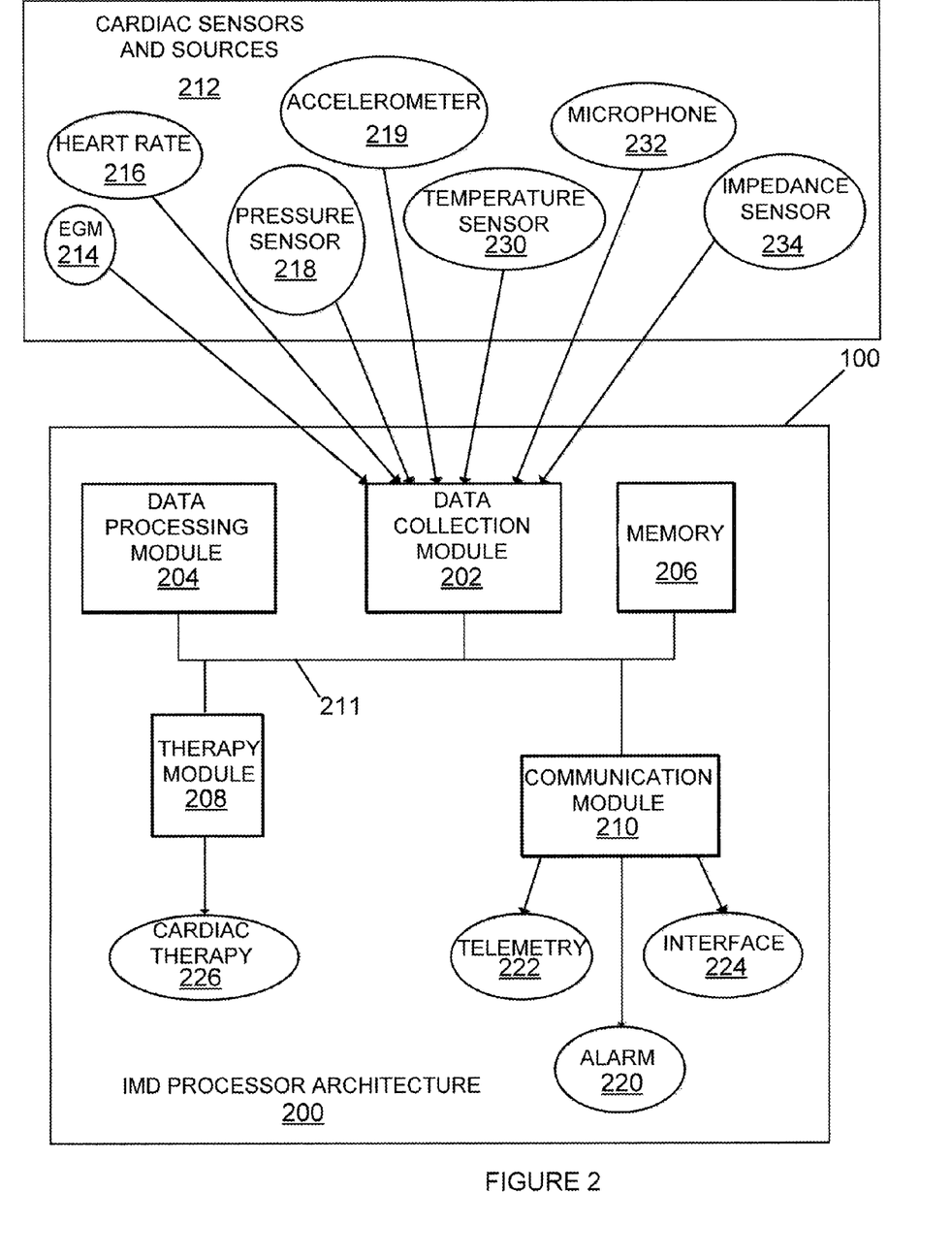
FIG. 2 is a schematic representation of a portion of an IMD configured in accordance with an embodiment of the present disclosure.

The following description refers to elements or features being "connected" or "coupled" together. As used herein, unless expressly stated otherwise, "connected" means that one element/feature is directly or indirectly connected to another element/feature, and not necessarily mechanically. Likewise, unless expressly stated otherwise, "coupled" means that one element/feature is directly or indirectly coupled to another element/feature, and not necessarily mechanically. Thus, although the schematic shown in FIG. 2 depicts one example arrangement of processing elements, additional intervening elements, devices, features, or components may be present in an actual embodiment (assuming that the functionality of the system is not adversely affected).

Figure 1:
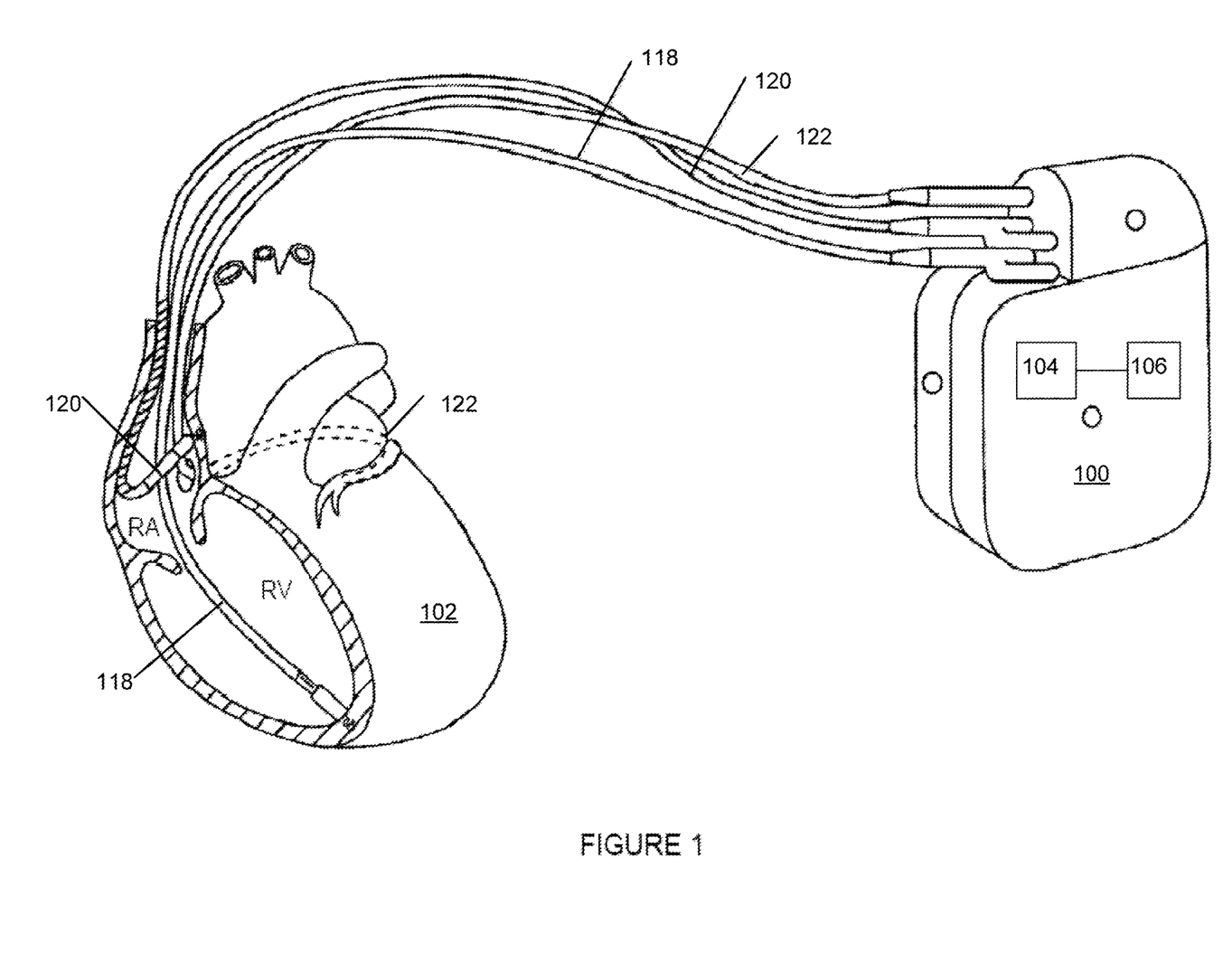
FIG. 1 is a schematic diagram of an implantable medical device (IMD) in accordance with an embodiment of the present disclosure.

FIG. 1 is an illustration of an exemplary implantable medical device (IMD) 100 connected to monitor a patient's heart 102. IMD 100 may be configured to integrate both monitoring and therapy features, as will be described below. IMD 100 collects and processes data about heart 102 from one or more sensors and an electrode pair for sensing cardiac electrogram (EGM) signals. IMD 100 may further provide therapy or other response to the patient as appropriate. As shown in FIG. 1, IMD 100 may be generally flat and thin to permit subcutaneous implantation within a human body, e.g., within upper thoracic regions or the lower abdominal region. IMD 100 is provided with a hermetically-sealed housing that encloses a processor 104, a digital memory 106, and other components as appropriate to produce the desired functionalities of the device. In various embodiments, IMD 100 is implemented as any implanted medical device capable of measuring the heart rate of a patient and a ventricular or arterial pressure signal, including, but not limited to a pacemaker, defibrillator, electrocardiogram monitor, blood pressure monitor, drug pump, insulin monitor, or neurostimulator. In some embodiments, the IMD 100 can be a pacemaker system including a hemodynamic sensor together with memory function and software download capability for optimization algorithms.

Processor 104 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 104 executes instructions stored in digital memory 106 to provide functionality as described below. Instructions provided to processor 104 may be executed in any manner, using any data structures, architecture, programming language and/or other techniques. Digital memory 106 is any storage medium capable of maintaining digital data and instructions provided to processor 104 such as a static or dynamic random access memory (RAM), or any other electronic, magnetic, optical or other storage medium.

As further shown in FIG. 1, IMD 100 may receive one or more cardiac leads for connection to circuitry enclosed within the housing. In the example of FIG. 1, IMD 100 receives a right ventricular endocardial lead 118, a left ventricular coronary sinus lead 122, and a right atrial endocardial lead 120, although the particular cardiac leads used will vary from embodiment to embodiment. In addition, the housing of IMD 100 may function as an electrode, along with other electrodes that may be provided at various locations on the housing of IMD 100. In alternate embodiments, other data inputs, leads, electrodes and the like may be provided. Ventricular leads 118 and 122 may include, for example, pacing electrodes and defibrillation coil electrodes (not shown) in the event IMD 100 is configured to provide pacing, cardioversion and/or defibrillation. In addition, ventricular leads 118 and 122 may deliver pacing stimuli in a coordinated fashion to provide biventricular pacing, cardiac resynchronization, extra systolic stimulation therapy or other therapies.

IMD 100 suitably collects and processes data about heart 102 from one or more sources (e.g., heart rate monitor, blood pressure monitor etc.). IMD 100 can obtain EGM data input from at least one electrode that is carried by a lead, such as right ventricular endocardial lead 118, or from a lead-less electrode. The right ventricular lead 118 can provide a real-time electrical signal to IMD 100 from the right ventricle of heart 120. The electrode may be contained on an independent lead, or may be integrated into a pacing or defibrillation lead. In alternate embodiments, other data inputs, leads, electrodes and the like may be provided. The right ventricular lead 118 may include, for example, pacing electrodes and defibrillation coil electrodes (not shown) for purposes of pacing, cardioversion, and/or defibrillation. In various embodiments, EGM data can be acquired from signals sensed by subcutaneous electrodes, epicardial electrodes, transvenous or endocardial electrodes, or a neurostimulation lead. In one embodiment, subcutaneous ECG signals can be substituted for EGM signals. IMD 100 may also obtain input data from other internal or external sources (e.g., as shown in FIG. 2) such as an oxygen sensor, pH monitor, accelerometer or the like.

In operation, IMD 100 obtains data about the heart 102 via the leads 118, 120, 122, and/or other sources. This data is provided to processor 104, which suitably analyzes the data, stores appropriate data in memory 106, and/or provides a response or report as appropriate. In particular, IMD 100 generates one or more therapy signals that are preferably optimized in accordance with the obtained data. In the example embodiment, IMD 100 detects myocardial ischemia and delivers an appropriate therapy or generates an alert.

Any identified cardiac episodes (e.g., an arrhythmia or heart failure decompensation) can be treated by intervention of a physician or in an automated manner. In various embodiments, IMD 100 activates an alarm upon detection of an ischemic event. Alternatively or in addition to alarm activation, IMD 100 selects or adjusts a therapy and coordinates the delivery of the therapy by IMD 100 or another appropriate device. Optional therapies that may be applied in various embodiments may include drug delivery or electrical stimulation therapies such as cardiac pacing, cardiac resynchronization therapy, extra systolic stimulation, and neurostimulation.

FIG. 2 is a schematic representation of a portion of an IMD 100 configured in accordance with an example embodiment of the present disclosure. In particular, FIG. 2 depicts an exemplary data processing layout for an IMD processor architecture 200, which may be located within the housing of a suitable IMD as described herein. In this example, processor architecture 200 includes at least a data collection module 202, a data processing module 204, a suitable amount of memory 206, a therapy module 208, and/or a communication module 210. These modules may be coupled to each other via a suitable data communication bus or arrangement 211. Each of the various modules may be implemented with computer-executable instructions stored in memory 206 and executing on processor architecture 200, or in any other practical manner. The exemplary modules and blocks shown in FIG. 2 are intended to illustrate one logical model for implementing an IMD in accordance with the invention, and should not be construed as limiting. Indeed, the various practical embodiments may have widely varying software modules, data structures, applications, processes and the like. As such, the various functions of each module may in practice be combined, augmented, optimized or otherwise differently-organized in any fashion.

In accordance with the practices of persons skilled in the art of computer programming, the present disclosure may be described herein with reference to symbolic representations of operations that may be performed by the various computing components, modules, or devices. Such operations are sometimes referred to as being computer-executed, computerized, software-implemented, or computer-implemented. It will be appreciated that operations that are symbolically represented include the manipulation by the various microprocessor devices of electrical signals representing data bits at memory locations in the system memory, as well as other processing of signals. The memory locations where data bits are maintained are physical locations that have particular electrical, magnetic, optical, or organic properties corresponding to the data bits.

When implemented in software or firmware, various elements of the IMDs described herein are essentially the code segments or instructions that perform the various tasks. The program or code segments can be stored in a processor-readable medium or transmitted by a computer data signal embodied in a carrier wave over a transmission medium or communication path. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a hard disk, a fiber optic medium, or the like. The computer data signal may include any signal that can propagate over a transmission medium such as electronic network channels, optical fibers, air, electromagnetic paths, or RF links.

Data collection module 202 suitably interacts with one or more data sources 212 to obtain data about the patient. Data sources 212 include any source of information about the patient's heart and possibly other physiologic information. In various embodiments, data sources 212 may include an EGM source 214 that provides electrical impulses or other observed signals that can be used to model the patient's EGM waveform. Other data sources 212 may include a heart rate sensor 216, a pressure sensor or monitor 218, an accelerometer 219, a temperature sensor 230, a microphone 232, and an impedance sensor 234. In practice, an IMD may also utilize a sensor for determining cardiac conduction time, blood pH sensors, and/or other known data sources. The various data sources 212 may be provided alone or in any combination with each other, and may vary widely from embodiment to embodiment.

The data collection module 202 suitably receives data from each of the data sources 212 by polling each of the data sources 212, by responding to interrupts or other signals generated by the data sources 212, by receiving data at regular time intervals, or according to any other temporal scheme. In particular, the data collection module 202 is configured to obtain an intracardiac EGM signal from the patient for processing. Data may be received at the data collection module 202 in digital or analog format according to any protocol. If any of the data sources 212 generate analog data, the data collection module 202 suitably translates the analog signals to digital equivalents using any form of analog-to-digital conversion scheme presently known or subsequently developed. The data collection module 202 may also convert data from protocols used by the data sources 212 to data formats acceptable to the data processing module 204, as appropriate. It should be appreciated that the EGM source 214, the processor architecture 200, the data collection module 202, and any corresponding logical elements, individually or in combination, are example means for obtaining an EGM signal of a patient as used herein.

The data processing module 204 is any circuit, programming routine, application or other hardware/software module that is capable of processing data received from the data collection module 202. In various embodiments, the data processing module 204 is a software application executing on processor architecture 200 to implement the processes described below. Accordingly, the data processing module 204 interprets received EGM signals, generates or analyzes signals based upon or derived from received EGM signals, and/or handles other data to adjust one or more operating parameters of the IMD 100.

In one embodiment, the data processing module 204 receives EGM signal data and/or other appropriate information from the data collection module 202 and interprets the data using digital signal processing techniques. For example, the data processing module 204 can calculate the ST-segment, T-wave amplitude, and T-wave alternans. In this regard, the data processing module 204, the processor architecture 200, and any corresponding logical elements, individually or in combination, are example means for generating ST-segment or T-wave signals based on the EGM signal.

The data processing module 204 is configured to identify at least one attribute of the EGM and/or at least one attribute of the ST-segment or T-wave signals based upon the EGM signal and correlate the identified attributes to determine the severity of myocardial ischemia in the patient. The EGM signal can be utilized as a feedback control mechanism to adjust the therapy delivered by the IMD 100. It should be appreciated that the data processing module 204, the processor architecture 200, and any corresponding logical elements, individually or in combination, are example means for identifying attributes of the EGM signal and/or the ST-segment or T-wave signals.

The communication module 210 is any circuit or routine that facilitates the transfer of data, information, reports, or programming instructions between the IMD 100 and an external device, system, or person (e.g., the patient, a physician, or a caregiver). In various embodiments, communication module 210 may be configured to generate an audible or visible alarm 220, handle wireless messages via a telemetry circuit 222, or manage the transmission of other data using any suitable interface 224. In this regard, the communication module 210 may facilitate open-loop feedback control of the IMD operating parameters by transmitting EGM signals or EGM signal attributes to an external processing system that responds with programming instructions to adjust the AV delay or other IMD parameters in the manner described herein. In some embodiments, the alarm 220 and/or the telemetry module 222 can be used to provide a warning feature for ischemia, an acute cardiac event, disease progression, cardiac reserve, exercise tolerance, and/or congestive cardiac failure.

The therapy module 208 is any suitable circuit, software application or other component that is configured to deliver cardiac therapy 226 to the patient. In the example embodiment, the therapy module 208 is configured to provide pacing as one form of cardiac therapy 226. In some embodiments, therapy module 208 may be alternatively or additionally configured to deliver various modes of pacing, post-extrasystolic potentiation, cardioversion, defibrillation and/or any other therapy. It should be appreciated that the therapy module 208, the cardiac therapy 226, the processor architecture 200, and any corresponding logical elements, individually or in combination, are example means for automatically the therapy signal generated by the IMD 100.

The various components and processing modules of the IMD 100 may be housed in a common housing such as that shown in FIG. 1. Alternatively, portions of the IMD 100 may be housed separately. For example, portions of the therapy module 208 could be integrated with the IMD 100 or provided in a separate housing. In this case, the therapy module 208 may interact with therapy electrodes via an electrical cable, wireless link, or the interface 224.

Figure 3:
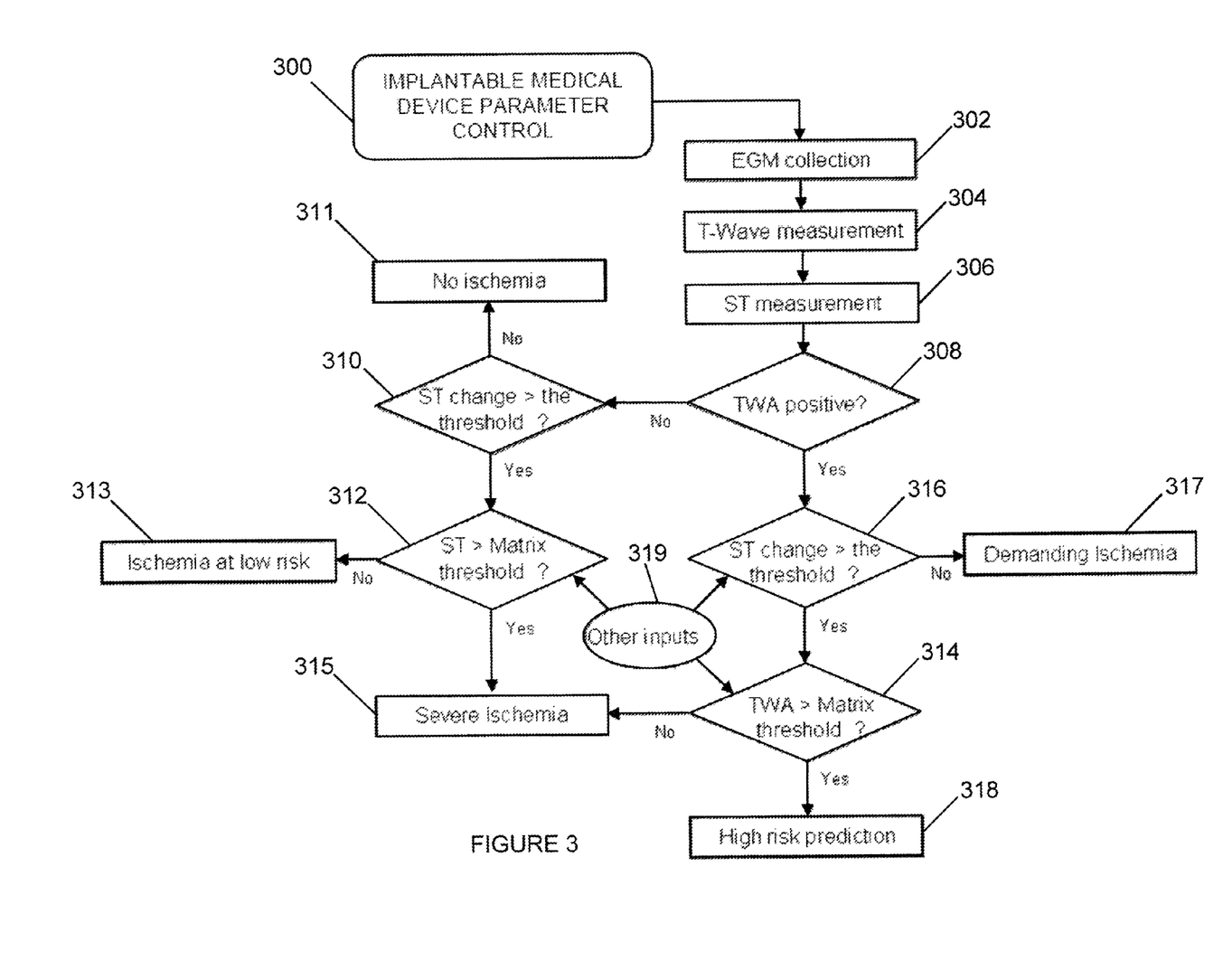
FIG. 3 is a flow chart of a method in accordance with one embodiment of the present disclosure.

TWA assessment in conjunction with ST segment deviations can provide the necessary information to determine the severity of myocardial ischemia and the condition of the heart (e.g., E/M dysfunction) to help predict VT/VF occurrence and prevent myocardial infarctions. For example, the detection of subtle TWA can indicate a moderate myocardial ischemia, the detection of significant TWA superimposed over an ST segment elevation/depression can indicate a significant myocardial ischemia and the formation of arrhythmogenic substrate, and the detection of complex TWA can strongly suggest an impending VT/VF. The magnitude of TWA and/or ST-segment deviations can also be accumulated for a time window, where sustained TWA and/or ST-segment deviations can also signify myocardial ischemia and E/M dysfunction. FIG. 3 is a flow diagram of an IMD parameter control process 300, which may be performed by an IMD 100 configured in accordance with an example embodiment of the present disclosure to determine the severity of myocardial ischemia.

The various tasks performed in connection with process 300 may be performed by software, hardware, firmware, or any combination thereof. For illustrative purposes, the following description of process 300 may refer to elements mentioned above in connection with FIGS. 1-2. In practical embodiments, portions of process 300 may be performed by different elements of the described system, e.g., data sources 212, processor architecture 200, or any component thereof. It should be appreciated that process 300 may include any number of additional or alternative tasks, some tasks shown in FIG. 3 need not be performed in the illustrated order, and process 300 may be incorporated into a more comprehensive procedure or process having additional functionality not described in detail herein.

IMD parameter control process 300 represents a method for analyzing a patient's EGM and detecting the severity of myocardial ischemia. Process 300 includes collecting or obtaining the EGM (task 302). EGM signals can be collected by selecting multiple unipolar and/or bipolar sensing electrode pairs, either simultaneously or sequentially. Both far-field and near-field EGM signals can be collected. Process 300 also includes measuring T-waves of the EGM (task 304) and ST segments of the EGM (task 306). Methods for acquiring T-wave signals are generally described in U.S. Patent Application Publication No. 2006/0116592, incorporated herein by reference in its entirety. Each T-wave measurement and ST segment measurement can be considered a single vector. The processor 104 can produce a T-wave matrix of sequential T-wave vectors and other secondary inputs and an ST matrix of sequential ST vectors and other secondary inputs in the memory 106.

Process 300 includes identifying TWA from the T-wave measurements (task 308). TWA assessment can be done by spectral analysis, modified moving averaging, or other averaging methods. In some embodiments, the TWA assessment is identified as positive when the alternans voltage deviates from a threshold value, such as about 10 micro-volts above the positive threshold value or about 10 micro-volts below the negative threshold value, depending on lead configuration, in one or more vectors. In other embodiments, TWA assessment can be performed by correlation analysis of individual beats relative to a median beat or other types of T-wave morphology analysis or the integration (i.e., accumulation) of TWA amplitudes over a specified time window. The integration of TWA amplitudes can be the product of the magnitude and the time.

If the TWA assessment is not positive (task 308), process 300 includes identifying ST segment deviations from the ST measurements (task 310). The ST segment assessment can be identified as positive when the ST segment level deviates above or below a threshold voltage, such as a deviation of about 0.1 milli-volts in one or more vectors. If the ST segment assessment is not positive (task 310), process 300 determines that no ischemia is present (task 311).

If the ST segment assessment is positive (task 310), process 300 performs ST segment matrix determinations (task 312). The severity of ischemia can depend on the level of ST segment elevation/depression and also the number of vectors with ST changes. By monitoring the ST segment deviations across a matrix of vectors, the severity of myocardial ischemia and E/M dysfunction can be determined. The ST segment matrix can also be analyzed by the integration (i.e., accumulation) of ST segment deviations over a specified time window (e.g., the product of the ST segment magnitude and time elapsed). For example, a large deviation seen in multiple ST segments or sustained significant ST segment elevation/depressions can indicate a more severe ischemia than a small deviation seen in a single vector or a small transient deviation seen in a specified time window. If the ST segment matrix determinations are not positive (task 312), process 300 determines that there is a low risk of ischemia (task 313). If the ST matrix determinations are positive (task 312), process 300 determines that severe ischemia is present (task 315).

If the TWA assessment is positive (task 308), process 300 includes identifying ST segment deviations from the ST measurements (task 316). The ST segment assessment can be positive when the ST segment level deviates above or below a threshold voltage, such as a deviation of about 0.1 milli-volts in one or more vectors. If the ST segment assessment is not positive (task 316), process 300 determines that demanding ischemia is present (task 317). If the ST segment assessment is positive (task 316), process 300 also performs TWA matrix determinations (task 314).

The TWA matrix determinations can help classify the severity of electrophysiological alternations caused by ischemia. Algorithms in the processor 104 can create a TWA matrix including the magnitude of the TWA amplitude, heart rate, the number of vectors with TWA positive, TWA continuity (i.e., the number of subsequent vectors with TWA positive), TWA integration (the product of TWA amplitudes and time elapsed), and the sign of the second order of TWA in order to determine the TWA severity. The sign of the second order of TWA relates to a triple beat alternans pattern, such as alternations between a first three vectors (beats 1, 2, and 3) and a subsequent three vectors (beats 4, 5, and 6), and/or determinations of waveform reversal patterns (analyzing beats 3 to 2 to 1 rather than beats 1 to 2 to 3). If the TWA matrix determinations are not positive (task 314), process 300 determines that severe ischemia is present (task 315). If the TWA matrix determinations are positive (task 314), process 300 determines that there is a high risk for sudden cell death and VT/VF occurrence (task 318). If extremely large TWA amplitudes are seen (task 314), process 300 determines that there is also a high risk for acute deterioration of myocardial contractile function (task 318).

In some embodiments of the invention, there are six possible paths that may be followed in the process 300.

Path 1: If the T-wave measurements are negative for TWA (i.e., task 308 is negative), and the ST segment measurements are less than or equal to the threshold (i.e., task 310 is negative), it is predicted that there is no ischemia in the patient's heart 102 (task 311).

Path 2: If the T-wave measurements are negative for TWA (i.e., task 308 is negative), the ST segment measurements are greater than the threshold (i.e., task 310 is positive), and the ST segment measurements are deemed below the matrix threshold (i.e., task 312 is negative), it is predicted that the patient's heart 102 is experiencing low risk ischemia (task 313).

Path 3: If the T-wave measurements are negative for TWA (i.e., task 308 is negative), and the ST segment measurements are greater than the threshold (i.e., task 310 is positive), and the ST segment measurements are deemed above the matrix threshold (i.e., task 312 is positive), it is predicted that the patient's heart 102 is experiencing severe ischemia (task 315).

Path 4: If the T-wave measurements are positive for TWA (i.e., task 308 is positive), the ST segment measurements are below or equal to the threshold (i.e., task 316 is negative), it is predicted that the patient's heart 102 is experiencing demanding ischemia (task 317).

Path 5: If the T-wave measurements are positive for TWA (i.e., task 308 is positive), the ST segment measurements are greater than the threshold (i.e., task 316 is positive), and TWA are deemed below or equal to the matrix threshold (i.e., task 314 is negative), it is predicted that the patient's heart 102 is experiencing severe ischemia (task 315).

Path 6: If the T-wave measurements are positive for TWA (i.e., task 308 is positive), the ST segment measurements are greater than the threshold (i.e., task 316 is positive), and TWA are deemed above the matrix threshold (i.e., task 314 is positive), it is predicted that the patient's heart 102 is at high risk for sudden cell death and VT/VF occurrence (task 318).

In conjunction with the above-mentioned six paths, secondary inputs 319 can be used to further predict the severity of the ischemia. Process 300 can also include measuring or obtaining secondary inputs 319 that include one or more of the following: heart rate, heart rate variability, number of premature ventricular contractions (PVC's), non-sustained ventricular tachycardia (NSVT), sustained ventricular tachycardia (SVT), time of day, electrocardiogram, patient activity, core body temperature, intra-cardiac impedance, intra-thoracic impedance, respiration rate, mixed venous oxygen saturation, wall contractility, wall tension, heart sounds, pulse oximeter data, and pulse pressure. Variables obtained from the secondary inputs 319 can be used within the ST segment matrix and TWA matrix to help distinguish, for example, demanding ischemia from supply ischemia. For example, a moderate ST segment elevation and low amplitude of TWA during fast sinus rate or high level of activity may suggest demanding ischemia. Other variables obtained in combination with matrix values may also help distinguish high-to-moderate or moderate-to-low ischemia.

In accordance with the example embodiment of the present disclosure, process 300 is associated with detecting ischemic cardiac events with a dual-chamber pacing device. Of course, process 300 may additionally (or alternatively) adjust IMD parameters, including, without limitation: pacing heart rate; AV delay timing; VV delay timing, which is the delay between pacing of both ventricles; AA delay timing, which is the delay between pacing of both atria; intra-atrium pacing delays for IMDs supporting multiple pacing leads in an atrium; intra-ventricle pacing delays for IMDs supporting multiple pacing leads in a ventricle; heart rate; lead location selection for IMDs supporting configurable activation of a plurality of leads in a single chamber (either the atrium and ventricle), which includes both therapy delivery and sensing leads. The IMD 100 can adjust the hemodynamic parameter or parameters (or can maintain its current operating status) in response to the EGM and/or ST segment and/or T-wave analysis. Of course, the specific adjustment mode, amount of adjustment, and frequency of adjustment will depend upon the current status of the patient, and the particular performance specifications of the IMD 100 itself.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method of detecting the severity of myocardial ischemia, the method comprising:
   obtaining an electrogram signal;
   determining T-wave measurements based on the electrogram signal;
   determining ST segment measurements based on the electrogram signal;
   identifying T-wave alternans based on the T-wave measurements;
   identifying ST segment changes based on the ST segment measurements;
   correlating the T-wave alternans with the ST segment changes; and
   detecting presence of ischemia and calculating a severity of the detected ischemia with a processor based at least on the correlation between the T-wave alternans and the ST segment changes.

2. The method of claim 1 wherein the severity of ischemia includes at least one of demanding ischemia, low-risk ischemia, severe ischemia, and high-risk ischemia.

3. The method of claim 1 wherein further comprising detecting a severity of at least one of myocardial electrical dysfunction and myocardial mechanical dysfunction based at least on the correlation between the T-wave alternans and the ST segment changes.

4. The method of claim 1 and further comprising obtaining a secondary input to detect the severity of ischemia and electrical/mechanical dysfunction, the secondary input including at least one of heart rate, heart rate variability, time of day, heart sounds, patient activity, impedance, core body temperature, respiration rate, mixed venous oxygen saturation, wall contractility, wall tension, pulse oximetry, pulse pressure, number of premature ventricular contractions, non-sustained ventricular tachycardia, and sustained ventricular tachycardia.

5. The method of claim 4 and further comprising creating a T-wave matrix including beat to beat T-wave measurements over a time period and the secondary input.

6. The method of claim 4 and further comprising creating a ST segment matrix of beat to beat ST segment measurements over a time period and the secondary input.

7. The method of claim 1 and further comprising detecting the formation of an arrhythmogenic substrate.

8. The method of claim 3 wherein the at least one of myocardial electrical dysfunction and myocardial mechanical dysfunction includes at least one of ventricular tachyarrhthmia, acute deterioration of myocardial contractile function and myocardial infarction.

9. The method of claim 1 wherein the ST segment changes are deviations beyond a threshold voltage.

10. The method of claim 1 wherein the T-wave alternans are identified by at least one of spectral analysis and averaging methods.

11. The method of claim 1 wherein the T-wave alternans are identified by at least one of statistical comparisons of subsequent median values of T-waves and accumulation of T-wave values over a specified time window.

12. An implantable medical device comprising:
a data collection module configured to obtain an electrogram signal;
a data processing module coupled to the data collection module,
the data processing module configured to determine T-wave alternans based on the electrogram signal;
the data processing module configured to determine ST segment changes based on the electrogram signal;
the data processing module configured to detect presence of ischemia and a severity of the detected ischemia based at least on correlation between the T-wave alternans and the ST segment changes; and
a therapy module coupled to the data processing module, the therapy module configured to at least one of deliver therapy and generate an alert indicating the severity of ischemia.

13. The device of claim 12 wherein the severity of ischemia includes at least one of demanding ischemia, low-risk ischemia, severe ischemia, and high-risk ischemia.

14. The device of claim 12 wherein the data processing module is further configured to detect at least one of myocardial electrical dysfunction and myocardial mechanical dysfunction based at least on the correlation between the T-wave alternans and the ST segment changes.

15. The device of claim 12 wherein the data collection module obtains a secondary input to detect the severity of ischemia, the secondary input including at least one of heart rate, heart rate variability, time of day, heart sounds, patient activity, impedance, core body temperature, respiration rate, mixed venous oxygen saturation, wall contractility, wall tension, pulse oximetry, pulse pressure, number of premature ventricular contractions, non-sustained ventricular tachycardia, and sustained ventricular tachycardia.

16. The device of claim 12 wherein the data processing module is further configured to detect ventricular tachyarrhthmia.

17. The device of claim 12 wherein the data processing module is further configured to detect the formation of an arrhythmogenic substrate.

18. The device of claim 12 and further comprising a data communication module coupled to the data collection module and the data processing module, the data communication module configured to wirelessly transmit at least one of the electrogram signal and attributes of the electrogram signal.

19. The device of claim 12 wherein the ST segment changes are deviations beyond a threshold voltage.

20. The device of claim 12 wherein the T-wave alternans are identified by at least one of spectral analysis, averaging and integration methods.

21. The method of claim 1, further comprising determining whether the T-wave alternans are superimposed over the ST segment and wherein detecting a severity of ischemia comprises detecting a severity of ischemia based on a level of the number of T-wave alternans that are superimposed over the ST segment.

22. The method of claim 1, further comprising:
accumulating a magnitude of the T-wave alternans for a time window; and
accumulating a magnitude of the ST segment changes for the time window;
wherein detecting a severity of ischemia comprises detecting the severity of the ischemia based on a level of the magnitude of the T-wave alternans and the ST segment changes during the time window.

23. The method of claim 1, further comprising
creating a ST segment matrix of beat to beat ST segment measurements over a time period; and
accumulating a magnitude of the ST segment changes;
wherein detecting the severity of ischemia comprises detecting the severity of ischemia based on the magnitude of the ST segment changes.

24. The method of claim 1, wherein correlating the T-wave alternans with the ST segment changes and detecting a severity of ischemia based at least on the correlation between the T-wave alternans and the ST segment changes includes:
determining whether the T-wave alternans are positive;
determining whether the ST segment changes are greater than a threshold; and
detecting demanding ischemia when the T-wave alternans are positive and the ST segment changes are not greater than the threshold.

25. The method of claim 24, further comprising:
producing a T-wave alternans matrix of sequential T-wave vectors;
determining whether the T-wave alternans is above a matrix threshold when the T-wave alternans are positive and the ST segment changes are greater than the threshold;
detecting severe ischemia when the T-wave alternans is not above the matrix threshold; and
detecting one of high risk for sudden cell death and VT/VF occurrence and high risk for acute deterioration of myocardial contractile function when the T-wave alternans is above the matrix threshold.

26. The method of claim 25, wherein the T-wave alternans matrix includes one or more of T-wave alternans amplitude, the number of vectors with T-wave alternans positive, the number of subsequent vectors with T-wave alternans positive, the product of T-wave alternans amplitudes and time elapsed, and the sign of the second order of T-wave alternans in order.

27. The method of claim 24, further comprising detecting no ischemia when the T-wave alternans are not positive and the ST segment changes are not greater than the threshold.

28. The method of claim 24, further comprising:
producing an ST matrix of sequential ST vectors;
determining whether the ST segment change is above an ST matrix threshold when the T-wave alternans are not positive and the ST segment changes are greater than the threshold;
detecting low risk of ischemia when the ST segment change is not above the ST matrix threshold; and
detecting severe ischemia when the ST segment change is above the ST matrix threshold.

29. The method of claim 24, wherein determining whether the T-wave alternan is positive when a T-wave alternans voltage exceeds a threshold.

30. The device of claim 12, wherein the data processing module is configured to determine whether the T-wave alternans are positive, determine whether the ST segment changes are greater than a threshold, and detect demanding ischemia when the T-wave alternans are positive and the ST segment changes are not greater than the threshold.

31. The device of claim 30, wherein the data processing module is configured to produce a T-wave alternans matrix of sequential T-wave vectors, determine whether the T-wave alternans is above a matrix threshold when the T-wave alternans are positive and the ST segment changes are greater than the threshold, detect severe ischemia when the T-wave alternans is not above the matrix threshold, and detect one of high risk for sudden cell death and VT/VF occurrence and high risk for acute deterioration of myocardial contractile function when the T-wave alternans is above the matrix threshold.

32. The device of claim 31, wherein the T-wave alternans matrix includes one or more of T-wave alternans amplitude, the number of vectors with T-wave alternans positive, the number of subsequent vectors with T-wave alternans positive, the product of T-wave alternans amplitudes and time elapsed, and the sign of the second order of T-wave alternans in order.

33. The device of claim 30, wherein the data processing module is configured to produce an ST matrix of sequential ST vectors, determine whether the ST segment change is above an ST matrix threshold when the T-wave alternans are not positive and the ST segment changes are greater than the threshold, detect low risk of ischemia when the ST segment change is not above the ST matrix threshold, and detect severe ischemia when the ST segment change is above the ST matrix threshold.

34. The device of claim 30, wherein the data processing module is configured to determine whether the T-wave alternan is positive when a T-wave alternans voltage exceeds a threshold.

35. A non-transitory machine-readable storage medium comprising computer-executable instructions that, when executed, cause a processor to:
  obtain an electrogram signal;
  determine T-wave measurements based on the electrogram signal;
  determine ST segment measurements based on the electrogram signal;
  identify T-wave alternans based on the T-wave measurements;
  identify ST segment changes based on the ST segment measurements;
  correlate the T-wave alternans with the ST segment changes; and
  detect presence of ischemia and a severity of the detected ischemia based at least on the correlation between the T-wave alternans and the ST segment changes.

* * * * *